United States Patent [19]

Siegel

[11] Patent Number: 5,062,841
[45] Date of Patent: Nov. 5, 1991

[54] IMPLANTABLE, SELF-REGULATING MECHANOCHEMICAL INSULIN PUMP

[75] Inventor: Ronald A. Siegel, San Francisco, Calif.

[73] Assignee: The Regents of the University of California, Berkeley, Calif.

[21] Appl. No.: 434,623

[22] Filed: Nov. 14, 1989

Related U.S. Application Data

[63] Continuation of Ser. No. 231,817, Aug. 12, 1988, abandoned.

[51] Int. Cl.$^5$ .............................................. A61K 9/22
[52] U.S. Cl. ................................. 604/891.1; 604/141; 424/423
[58] Field of Search .................. 604/891.1, 892.1, 131, 604/132, 141, 151, 153, 422, 423, 438; 424/422, 423, 438

[56] References Cited

U.S. PATENT DOCUMENTS

| | | | |
|---|---|---|---|
| 3,995,632 | 12/1976 | Nakano et al. | 604/892.1 |
| 4,209,014 | 6/1980 | Sefton | 604/891.1 |
| 4,717,566 | 1/1988 | Eckenhoff et al. | 604/892.1 |
| 4,723,958 | 2/1988 | Pope et al. | 604/891.1 |
| 4,820,273 | 4/1989 | Reinke | 604/141 |

OTHER PUBLICATIONS

Albisser, "Devices for the Control of Diabetes Meltius," Proc. IEEE (1979), 67:1308–1319.
Kim et al., "Self-Regulating Insulin Delivery Systems. 1. Synthesis and Characterization of Glycosylated Insulin," *J. Controlled Release* (1984), 1:57–66.
Kim et al., "Self-Regulating Insulin Delivery Systems. II. In Vitro Studies," *J. Controlled Release* (1984), 1:67–77.
Kim. et al., "Self-Regulating Insulin Delivery Systems. III. In Vivo Studies," *J. Controlled Release* (1984), 2:143–152.
Fischel-Ghodsian et al., "Enzymatically Control Drug Delivery," Proc. Natl. Acad. Sci. USA (1988), 85:2403–2406.
Heller et al., "A Bioerodible Self-Regulated Insulin Delivery Device," Proc. 13th Intl. Symp., *Controlled Release of Bioactive Materials*, 37–8 (1986).
Kost et al., "Glucose-Sensitive Membranes Containing Glucose Oxidase: Active Swelling, and Permeability Studies," *J. Biomed. Mater. Res.* (1985), 19:1117–11.
Albin et al., "Theoretical and Experimental Studies of Glucose Sensitive Membranes," *J. Controlled Release* (1987), 6:267–291.
Ishihara et al., "Glucose Induced Permeation Control of Insulin through a Complex Membrane Consisting of Immobilized Glucose Oxidase and a Poly(amine)," *Polymer Journal* (1984), 16:625–631.
Ishihara et al., "Glucose-Responsive Insulin Release from Polymer Capsule," *J. of Polymer Science: Polymer Letters Ed.* (1986), 24:413–417.

Primary Examiner—Stephen C. Pellegrino
Assistant Examiner—Michael Rafa
Attorney, Agent, or Firm—Townsend and Townsend

[57] ABSTRACT

An implantable pump for the delivery of insulin to a mammal has a biocompatible housing which supports an aqueous-swellable glucose-sensitive member and a chamber containing a pharmaceutically acceptable insulin composition. The aqueous-swellable member is exposed to the body fluids which surround the pump when it is implanted; it initiates an insulin pumping cycle by swelling in response to an increase in blood glucose level and terminates an insulin pumping cycle by deswelling in response to the decrease in blood glucose level. When the glucose-sensitive aqueous-swellable member swells in response to an increase in blood glucose level, it generates a hydraulic force which causes insulin composition to be expelled from the chamber through a pressure-sensitive one way valve. The valve seals the chamber when the hydraulic force is withdrawn by deswelling of the glucose-sensitive aqueous-swellable member.

44 Claims, 3 Drawing Sheets

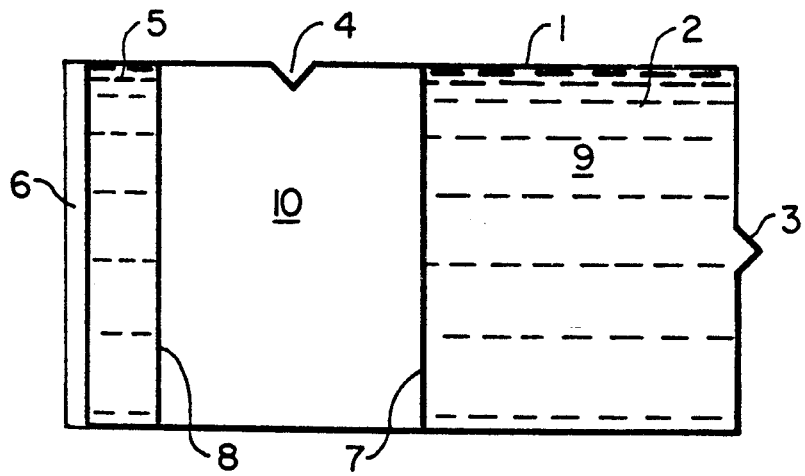
FIG._1A.
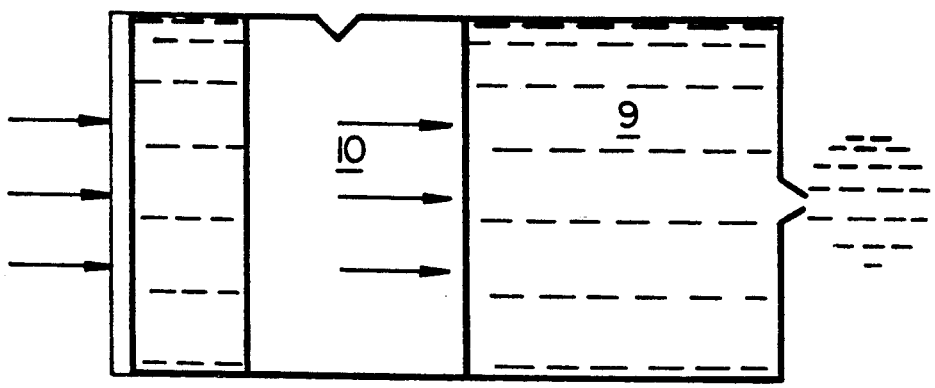
FIG._1B.
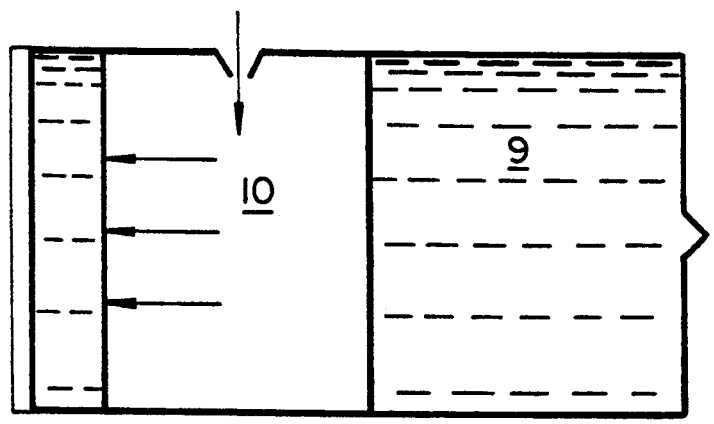
FIG._1C.

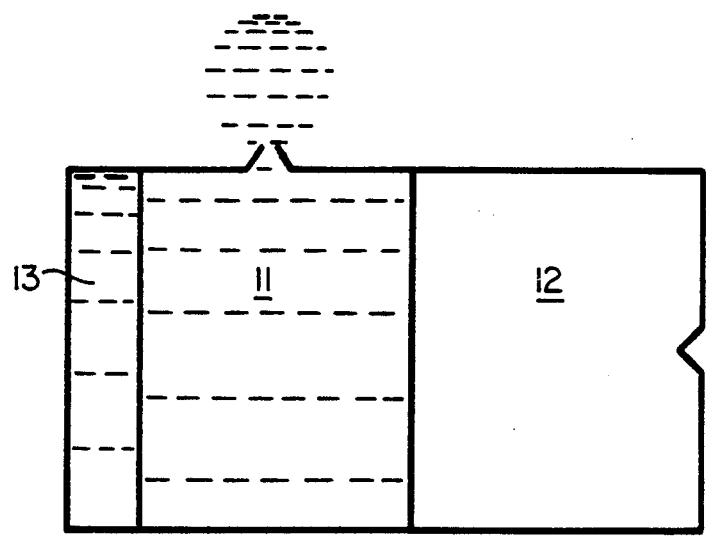
FIG._2.
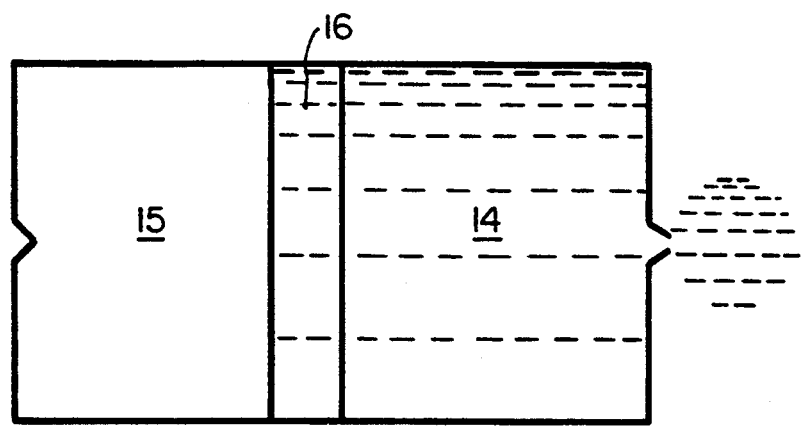
FIG._3.

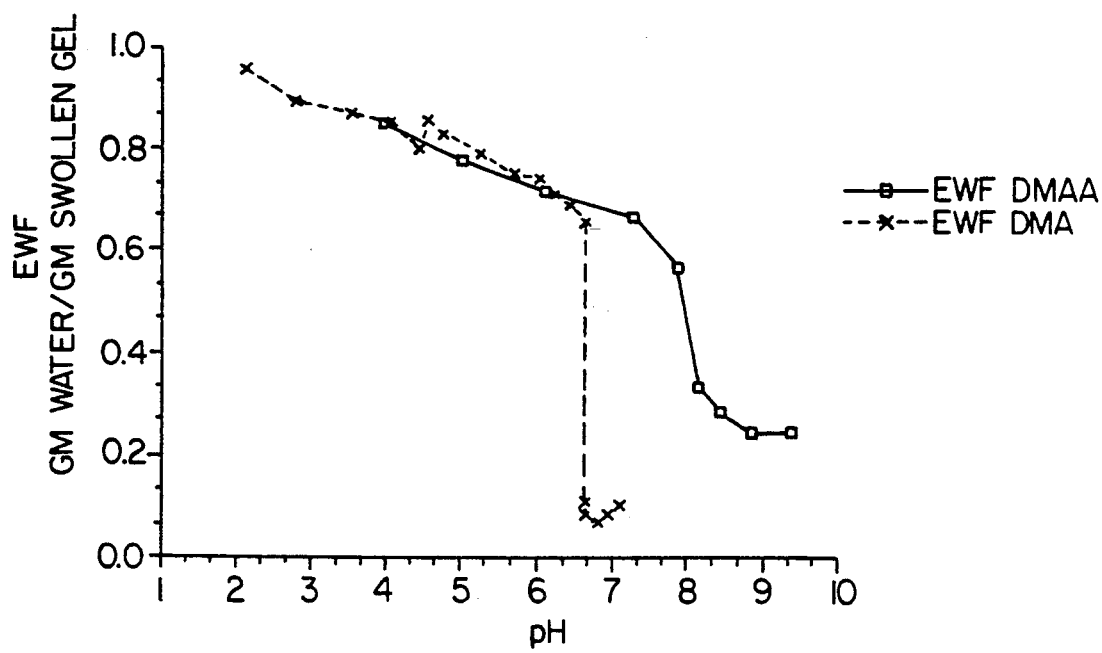
FIG._4.
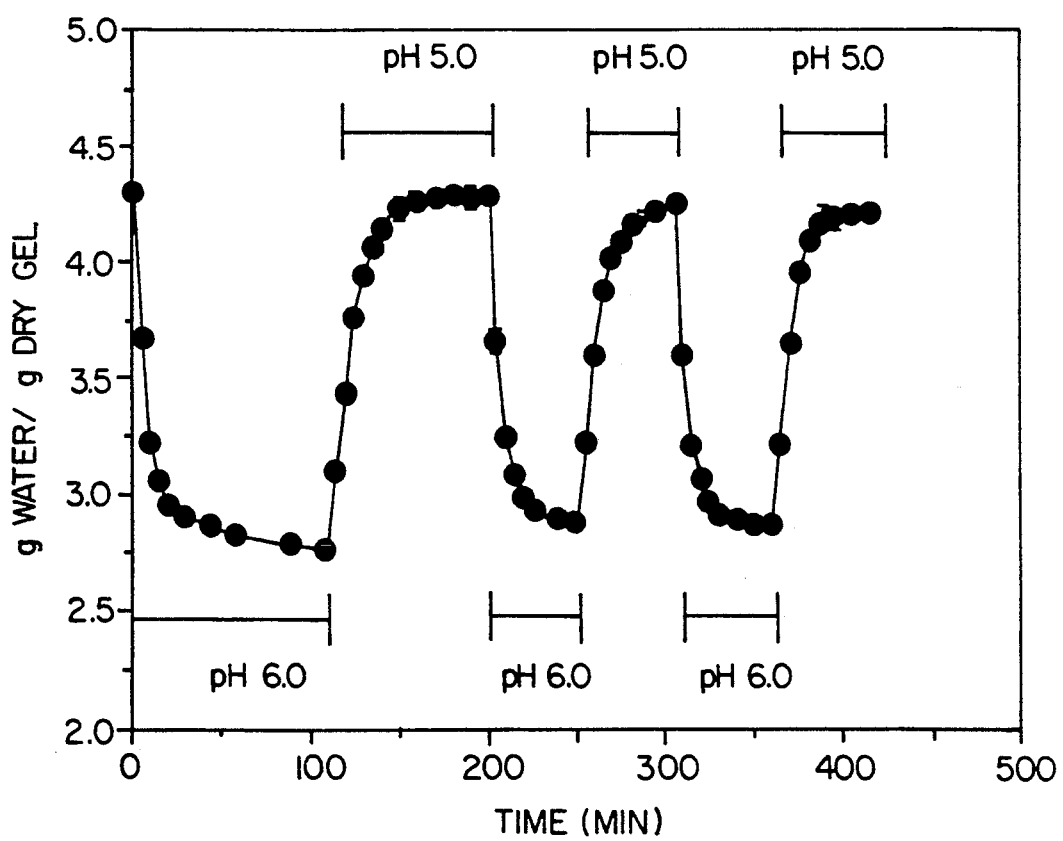
FIG._5.

IMPLANTABLE, SELF-REGULATING MECHANOCHEMICAL INSULIN PUMP

This is a continuation of application Ser. No. 231,817, filed Aug. 12, 1988, now abandoned.

BACKGROUND OF THE INVENTION

1. Field of the Invention

This invention relates to a self-regulated implantable pump for the delivery of insulin to diabetic mammals, particularly humans, in response to their insulin needs. Specifically, it relates to a mechanochemical pump which, when implanted in a mammal, delivers insulin by hydraulic force in direct and proportionate response to an increase in the blood glucose level of the mammal in which it is implanted.

Approximately two million Americans are insulin dependent diabetics. After heart disease and cancer, diabetes is the third leading cause of death in the United States. It is also the leading cause of blindness in the U.S., and a major cause of neuropathy, nephropathy and atherosclerosis. Before the isolation of insulin in 1921 by Banting and Best, insulin dependent diabetics usually died within four years of onset due to the inability to efficiently utilize glucose as an energy source, and the ketoacidosis which arises from breaking down fat for energy. The introduction of insulin therapy has substantially eliminated the acutely lethal aspects of insulin dependent diabetes. Mortality, however, remains high, due primarily to the longer term impact of the degenerative conditions listed above.

2. Description of Related Art

Presently, the most common route of insulin delivery is by subcutaneous injection. This procedure is inconvenient to the patient, and is probably not optimal from a therapeutic standpoint. Blindness, neuropathy and nephropathy are caused by the thickening of capillary basement membranes in the corresponding organs. This, as well as atherosclerosis, stems from a general hyperglycemia which results from the fact that the release of subcutaneously injected insulin does not mimic the release pattern of insulin from a healthy pancreas. Diabetics can bring their blood sugar level down into the normal range by careful control of diet. However, in this case there is always the danger that blood sugar will drop below acceptable levels (hypoglycemia), which is a dangerous condition.

The normal pancreas releases insulin at a rate determined by blood sugar level. By this method the nondiabetic body exercises closed loop control of blood sugar. In contrast, subcutaneous injection is clearly an open loop strategy, which explains the suboptimal glycemia control that is achieved. As a result, diabetics are usually hyperglycemic.

It has been hypothesized that the long term degenerative complications of diabetes might be averted if blood glucose levels could be reduced. This could be accomplished by an implantable, self-regulating insulin delivery system. In addition, such a system would eliminate the inconvenience of regular injections, albeit at the cost of requiring occasional surgery. The present goal is to develop an implantable system that could provide self-regulated delivery for a period of six months to one year.

Several research groups have developed insulin delivery systems that attempt to mimic the closed loop aspect of the normal pancreas. These can be classified as electromechanical and chemical. The electromechanical devices generally require an electrochemical glucose sensor which signals to an electromechanical actuator that pumps glucose. In chemical systems, no electrical component exists, and the sensing of glucose and transduction to insulin release rate are coupled solely by chemical processes.

To date the most fully developed system for closed-loop insulin delivery is the electromechanical "artificial beta cell," developed by Albisser and colleagues [Proc. IEEE 67, 1308 (1979)]. This is an experimental bedside system. The patient's blood is sampled by a catheter and analyzed continuously for glucose. Glucose levels are fed into a computer which then determines the insulin delivery rate. Insulin delivery is actuated by a peristaltic pump feeding a second catheter to the patient. This system is mainly an experimental tool, since the collective bulk of all components, plus the need for a cutaneous catheter, preclude its use with ambulatory patients.

Attempts to miniaturize this and other electromechanical systems for in vivo implantation have been thwarted by the unavailability of a chronically implantable glucose sensor. It is not expected that this problem will be solved in the near future. Even if miniaturization were possible, certain drawbacks would remain for any electromechanical system. A miniaturized artificial beta cell would be either wearable or implanted. Wearable systems, although doubtless an improvement over injections, necessarily involve a cutaneous junction which is inconvenient, and a potential locus for infection if great care is not taken. Implantable electromechanical systems also require a power source, which takes up considerable volume, plus many moving parts, all of which are subject to failure.

The potential problems with electromechanical insulin delivery have led several groups of researchers to consider chemical means to provide closed-loop insulin delivery. Kim and colleagues [J. Controlled Release 1, 57 (1984), J. Controlled Release 1, 67, (1984) and J. Controlled Release 2, 143 (1985)] have designed a system that takes advantage of the fact that glycosylated insulin bound to the plant lectin concanavalin A (ConA) is displaced by glucose. A device was developed consisting of a macroporous, hydrophilic membrane surrounding a solution of ConA/glycosylated insulin. When blood glucose level rises, glucose crosses the membrane and displaces the glycosylated insulin from the ConA. The released insulin diffuses through the membrane into the blood. However, a potential problem with this system is the use of glycosylated insulin and ConA, each of which may induce an immunogenic response.

Another idea has been pursued by Ghodsian, et al. [Proc. Natl. Acad. Sci. 85, 2403 (1988). A mixture of the immobilized enzymes glucose oxidase (GluOx) and catalase (Cat), and a chemically derivatized form of insulin (trilysil insulin) was incorporated into a porous polymer matrix. The enzymes convert glucose oxidase into gluconic acid, causing a local drop in pH within the pores of the polymer matrix. Since the solubility of trilysil insulin is minimal at neutral pH (7.4), and increases rapidly with decreasing pH, an increase in insulin solubility and therefore release is the ultimate result of an increase in glucose concentration. In principle this system can provide closed loop control. At present there appear to be two disadvantages to this approach, however. First, the suitability of trilysil insulin for long term use has not been established. Unmodified human, porcine or bovine insulins cannot be used, since their solubility-pH profiles are not correct. Second, the response time becomes slower with each burst of insulin. This is because release occurs at a "moving front" which separates solid insulin from pore water. With time, this front continuously recedes into the matrix, and more time is required for glucose and H+ to diffuse in the pores to the insulin, and for insulin to diffuse out of the pores.

A third polymer-based chemically selfregulating system has been pursued by Heller [Proc. 13th Intl. Symp. Controlled Release of Bioactive Materials, p. 35 (1986)]. In this system, insulin is imbedded into a hydrophobic polymer which undergoes surface erosion. As the polymer erodes, insulin at and just below the surface is released. The polymer is chosen such that the erosion rate is small at neutral pH but increases as pH decreases. Again, change in pH is triggered by the GluOx/Cat reaction.

Yet another approach is being pursued by Horbett, et al. [J. Biomed. Mater. Res. 19, 1117 (1985) and J. Controlled Release 6, 267 (1987)], and Ishihara, et al. [Polymer J. 16, 625 (1984)]. These research groups have developed cross-linked hydrogel membranes whose permeability to insulin is pH sensitive. Permeability change is due to swelling of the polymer and "opening of pores." The swelling in turn is due to protonation of amine groups residing on the sidechains of the polymer as a result of the pH-lowering effect of the glucose/glucose oxidase reaction. Practical implementation of these membranes would involve an aqueous insulin reservoir surrounded by the permeable membranes. However, with this system, any insulin degradation and aggregation which occur over time could lead to inactivation of the drug and clogging of the membrane.

Thus, while the concept of utilizing the reaction of blood glucose with glucose oxidase to trigger a pH-responsive delivery of insulin is known, the art available insulin delivery mechanisms which utilize this reaction require the transport of insulin from and through the very matrices and membranes in which the glucose/glucose oxidase reaction takes place. As a result, the self-regulating delivery properties of these matrices and membranes are highly susceptible to deposits of insulin degradation products, and in the case of the matrix, suffer from delivery kinetics which slow with time due to the geometry of the matrix and the receding insulin front.

SUMMARY OF THE INVENTION

The present invention is directed to a new self-regulated mechanochemical insulin pump which employs a water-swellable hydrogel that swells in response to an increase in blood glucose level, and deswells in response to a decrease or normalization of blood glucose level. Instead of exploiting changes in insulin permeability of the hydrogel due to swelling, this invention uses the hydraulic force generated by swelling to "pump" insulin out of a separate reservoir in response to changes in blood glucose level.

The pump of this invention functions as an artificial pancreas, delivering insulin to diabetic patients at a rate that is modulated by blood glucose level. It obviates the need for insulin injections, and provides superior control of glycemia, since it simulates a normal pancreas more closely than is possible with a regimen of injections. The implantable insulin delivery device functions by converting chemical energy from blood glucose to a mechanical pumping force, hence the term "mechanochemical." It does not require an internal power source, which is a distinct advantage of this strategy over the electromechanical approaches that have been proposed by others. Furthermore, it does not rely on release of insulin from a pH-sensitive matrix or membrane, the properties of which can change significantly over time due to chemical processes associated with the transport of insulin through the matrix or membrane.

In one aspect, this invention provides an implantable pump for the delivery of insulin to a mammal in need thereof, comprising a housing which supports within its walls:

(a) an aqueous-swellable member which initiates an insulin pumping cycle by swelling in response to an increase in blood glucose level and terminates an insulin pumping cycle by deswelling in response to a decrease in blood glucose level, said member being exposed to the body fluids which surround the pump when implanted in a mammal;

(b) a first chamber containing a pharmaceutically acceptable insulin composition and including a valve means which permits the outflow of the insulin composition; and (c) means coupled with said first chamber for causing insulin to be expelled from the first chamber in response to swelling of the aqueous-swellable member.

In another aspect, this invention provides an implantable pump for the delivery of insulin to a mammal in need thereof, comprising an implantable, biocompatible housing of fixed volume which supports within its walls:

(a) an aqueous-swellable hydrogel member which swells in response to an increase in blood glucose level and deswells in response to a decrease in blood glucose level, said member being exposed to the body fluids which surround the pump when implanted in a mammal;

(b) means defining a first chamber for holding a pharmaceutically acceptable insulin formulation, including a valve-means which permits the outflow of the insulin composition;

(c) means defining a second chamber for coupling the swelling of the aqueous-swellable hydrogel member to the first chamber such that insulin composition is expelled from the first chamber in response to swelling of the aqueous-swellable hydrogel member.

In yet another aspect, the pump of this invention comprises an implantable, biocompatible housing of fixed volume which supports within its walls:

(a) a first chamber containing a pharmaceutically acceptable insulin composition and including a pressure-responsive valve means which permits the outflow of the insulin composition in response to an increase in pressure in the chamber and seals the chamber in response to a decrease in pressure in the chamber; and (b) a second chamber including a pressure-responsive valve means which seals the chamber in response to an increase in pressure in the chamber, and permits an influx of body fluids in response to a decrease in pressure in the chamber;

(c) an aqueous-swellable hydrogel member which initiates an insulin pumping cycle by swelling in response to an increase in blood glucose level and terminates an insulin pumping cycle by deswelling in response to a decrease in blood glucose level, said member being exposed to the body fluids which surround the pump when implanted in a mammal and including a coupling means adjacent to at least one of said first and second chambers such that swelling of the hydrogel member causes an increase in pressure in both chambers.

The pump of this invention provides several significant advantages over the previously known electrochemical and chemical pumps. By converting chemical energy to mechanical energy, the present invention provides a self-regulating implantable insulin pump which does not require an electrical power source, a motor and associated electromechanical moving parts. As such, the pump of this invention is quite small, which provides great advantages for implantation. Unlike existing chemical systems, the insulin contained in the present pump is completely separated from the enzyme/polymer system. Therefore, the insulin can be formulated in a variety of ways that may be chosen to optimize stability of the insulin for long term implantation. Moreover, permeation of insulin through matrices and membranes is not required. Hence the present pump provides a self-regulation means which is not affected by problems arising from insulin aggregation and clogging of polymer membranes.

A major advantage of the implantable insulin pump of this invention is that insulin delivery is directly proportional to the swelling rate of the water-swellable hydrogel member. Thus the pump can respond rapidly to changes in blood glucose, providing optimal emulation of the responsive behavior of the normal pancreas.

BRIEF DESCRIPTION OF THE DRAWINGS

FIGS. 1A, 1B, 1C are schematics which depict an embodiment of the invention and its manner of operation in vivo as the blood glucose level of a patient in which it is implanted rises and falls.

FIG. 1(A) illustrates the pump in resting configuration prior to initiation of an insulin pumping cycle. FIG. 1(B) depicts the configuration and operation of the same pump as the blood glucose level rises and an insulin pumping cycle is initiated. FIG. 1(C) depicts the configuration of the same pump after the blood glucose level has decreased in response to the delivery of insulin.

FIG. 2 illustrates an embodiment of the invention in which the aqueous-swellable hydrogel member is in contact with the first chamber but not the second chamber.

FIG. 3 illustrates an embodiment of the invention in which the aqueous-swellable hydrogel member is positioned between the first and second chambers.

FIG. 4 shows the swelling isotherm for the MMA/DMA and MMA/DMAA 70/30 mole % gels prepared according to Example 1 as a function of pH at 25° C. and a total ionic strength of 0.1M. Citrate buffer (0.01M) was used at and below pH 7.0, and phosphate buffer (0.01M) was used above pH 7.0.

FIG. 5 shows the kinetics of swelling and deswelling of MMA/DMA 70/30 mole % copolymer discs in response to step changes in pH in a pH region (5.0–6.0) where the gel is already quite swollen.

DETAILED DESCRIPTION OF THE PREFERRED EMBODIMENTS

The self-regulating mechanochemical insulin pump of this invention is an implantable device that can automatically deliver insulin to diabetic patients in response to their insulin needs. By converting the chemical energy generated by the reaction of blood glucose with an immobilized enzyme into a hydraulic force which mechanically expels a portion of an insulin formulation from a reservoir in which it is stored, the pump of this invention derives both its self-regulation mechanism and its mechanical driving force directly from an increase in the blood glucose level of the diabetic patient in whom it is implanted. Insulin is delivered as a direct response to an increase in blood glucose level. Thus, the pump increases its insulin output when the patient's blood glucose level rises, and shuts off when the blood glucose level falls.

Since the proposed pump functions by converting chemical changes into hydraulic force, it is termed "mechanochemical." In the present system, work is produced by expansion of polymer gel, which causes the desired pumping to occur.

One embodiment of the self-regulated implantable insulin pump of this invention is illustrated in FIG. 1A. As shown, it comprises a housing (1), of fixed volume, which supports within its walls two chambers which are separated from each other by a movable partition (7). In the first (right-hand) chamber (9), an insulin-composition (2) is stored which may be pushed through a one-way pressure-responsive valve (3) when pressure inside chamber (9) exceeds the pressure in the environment (i.e., the body). The insulin formulation in Chamber (9) may be a solution, a suspension, a semi-solid, an emulsion, or any other pharmaceutically acceptable, flowable composition. The second (left-hand) chamber (10), is simply a fluid space. It communicates with the outside via a one-way pressure-responsive valve (4) that allows external fluids to flow into the chamber when pressure in the chamber is less than that in the environment of use. Thus, the influx of body fluids to the second chamber is a function of the expulsion of insulin composition from the first chamber. Adjacent to the chamber (10) is a diaphragm (8) which in turn is connected to a glucose-sensitive water-swellable hydrogel member (5). Finally, the hydrogel member is bounded by a screen (6) which permits exposure of the hydrogel to external fluids but allows swelling to occur only into the device.

As shown in FIG. 1B, the water-swellable hydrogel member swells under conditions of high blood glucose levels. When the gel swells (in response to increasing blood glucose), the diaphragm pushes against the chamber (10), closing valve (4). The excess pressure in the chamber (10) is relieved by pushing against chamber (9), forcing the insulin to exit through valve (3).

As shown in FIG. 1C, when the hydrogel deswells (in response to decreasing blood glucose), pressure in chamber (10) drops, valve (4) opens and external fluid flows into that chamber. In addition, the reduced pressure in the pump causes valve (3) to close so that no external fluid will flow into chamber (9) and dilute the insulin. As external fluids flow into the second chamber (10), it expands so that the combined total volume of the first and second chambers at normal resting pressure after completion of the insulin pumping cycle is the same as the total combined volume occupied by the two chambers prior to initiation of the pumping cycle.

It will be apparent that the invention can be embodied in numerous forms in addition to that shown in FIGS. 1A, 1B, 1C. The key elements of the invention are the glucose sensitive, aqueous-swellable member and the chamber which acts as a reservoir for the pharmaceutically acceptable insulin solution and isolates it from the chemical reactions which lead to swelling of the aqueous-swellable member. The aqueous-swellable member regulates and provides power to the pump by swelling in response to an increase in blood glucose level and deswelling in response to a subsequent decrease in blood glucose level. It includes a pH-sensitive hydrogel membrane and an immobilized reagent, preferably glucose oxidase, which reacts in response to the presence of glucose in the blood to cause a change in pH and consequent swelling of the member. The insulin containing chamber acts as an isolating reservoir for the insulin and provides a port for its delivery to the body. It is coupled to the aqueous-swellable member in such a way that insulin composition is expelled in response to swelling of the aqueous-swellable member. The insulin containing chamber is preferably configured so that its internal volume decreases proportionately with the volume of insulin composition expelled during each pumping cycle.

The valving system described herein provides a convenient and effective way of providing the pump with reproducible insulin dose delivery in response to a given rise in blood glucose level, while isolating the stored insulin composition in an environment protected from external body fluids. Preferably it operates to exclude external fluids from the insulin reservoir but permit the influx of external fluids into a second chamber while pressure in that chamber is negative, so that the combined total volumes of the first and second chambers at resting pressure (i.e. external body pressure) between pumping cycles remains constant. The second chamber, therefore, acts as a fluid space which expands via the influx of body fluids. In a preferred embodiment, a pressure-responsive valve in the second chamber permits the influx of body fluids in a volume approximately equal to the volume of insulin composition expelled during each insulin pumping cycle. Further, the first and second chambers are preferably configured such that the influx of body fluid from the second chamber permits the total combined volume occupied by the first and second chambers within the housing to remain approximately the same, even after the insulin composition content of the first chamber has been substantially depleted as a result of repeated insulin pumping cycles. The constancy of the combined volumes of the first and second chambers is best determined when the pressure in both chambers equals the pressure of the environment external to the pump. It is also preferable that the internal volume of the first chamber is approximately the same as the volume of the insulin composition it contains, and is collapsible such that its internal volume stays approximately the same as the volume of the insulin composition remaining in the chamber after each pumping cycle.

Referring now to FIG. 2, another embodiment of the invention is illustrated in which the aqueous-swellable member (13) is positioned adjacent to the first chamber but not the second chamber. In this embodiment it is preferable that the aqueous-swellable member be fixed in its position within the housing.

Referring now to FIG. 3, an implantable, self-regulating insulin pump of the invention is shown in which the aqueous-swellable hydrogel member is positioned between the first and second chambers. In this embodiment, the aqueous-swellable member is preferably movably mounted within the housing, thus allowing the second chamber to expand as a function of the depletion of the first chamber as insulin is delivered therefrom.

The water-swellable hydrogel member may be a composite membrane, comprising a layer containing immobilized glucose oxidase, and a pH-sensitive gel layer that swells with a decrease in local pH. Alternatively, the water-swellable hydrogel member may be a monolayer comprising the immobilized glucose oxidase in a pH-sensitive hydrogel membrane. Preferably, the hydrogel member will be in a swollen state when the patient's glucose level is normal, and will respond rapidly and reproducibly to small perturbations in external pH, either increasing or decreasing its degree of swelling as the patient's blood glucose level changes.

In general, the hydrogels suitable for forming the water-swellable member are lightly cross-linked polybasic polymer gels. They swell in water and aqueous fluids, retain a significant volume of fluid within their structures, and are not water-soluble. When the water-swellable polymeric material is both cross-linked and contains weakly basic pendant groups, the sorption of water that occurs in aqueous solution can give rise to ionization of these pendant groups, altering the osmotic balance of the gel with respect to the aqueous fluid through ion exchange. As a result, the hydration, or equilibrium swelling of the hydrogel can be quite sensitive to pH of the external solution, and rapid, reproducible and reversible swelling can occur in response to a decrease in solution pH.

The hydrogels suitable for use in this invention can be of plant, animal or synthetic origin. Suitable hydrogel polymer materials include, but are not limited to, the poly(acrylic) and poly(methacrylic) acids and their derivatives, poly(N-vinyl-2-pyrrolidine) and its derivatives, and formaldehyde, glutaraldehyde and derivatives thereof.

The hydrogel is preferably selected so that it is substantially swollen in an equilibrium state at or near physiologic pH, and undergoes rapid and repeatable swelling and deswelling in response to changes in pH below the physiologic level. Hydrogels particularly suited for this purpose are homo- and copolymers of hydrophobic monomers selected from the n-alkyl acrylic and methacrylic acids, esters and amides, and the mono- and di-hydroxy and amino derivatives thereof, wherein n represents the number of hydrocarbon groups in the alkyl side chain and is an integer of 0–22. Examples of such monomers suitable for use in the aqueous-swellable hydrogel member include methylmethacrylate, ethylmethacrylate, glyceryl methacrylate, N-N dimethylaminoethyl methacrylate, N-N diethylaminoethyl methacrylate and N-N dimethylaminoethyl methacrylamide are well known in the literature as MMA, EMA, HEMA, HPMA, GMA, DMA, DEA and DMAA, respectively. Alternatively, a hydrophobic monomer such as, for example, DMA, can be copolmerized with a hydrophilic monomer such as 2-hydroxyethylmethacrylate, or 2-hydroxypropylmethacrylate, which are known in the literature as HEMA and HPMA, respectively.

In general, the hydrogels suitable for forming the aqueous-swellable member are made either by the polymerization or copolymerization of hydrophobic monomers, preferably with a cross-linking agent, or by the copolymerization of a mixture of hydrophilic monomers or polymers with hydrophobic monomers or polymers, also preferably with a cross-linking agent. Examples of suitable cross-linking agents include divinylbenzene, glycidyl acrylate, glycidyl methacrylate and glycidal crotonate. Divinylbenzene is a preferred cross-linking agent. Methods of polymerizing and copolymerizing hydrogels of the type suitable for use in this invention are well known to those of skill in the art. For example, suitable methods for preparing homo and copolymers of the n-alkyl acrylic and methacrylic acids, acrylates and acrylamides, the N-vinyl pyrolidines and the polyformaldehydes and polyglutaraldehydes are described in the Kirk-Othmer *Encyclopedia of Chemical Technology*, Third Edition, 198, published by John Wiley and Sons. Typically they are prepared by conventional radical bulk polymerization or copolymerization in the presence of the cross-linking agent and polymerization initiator such as 2,2'-azobisisobutyronitrile (ABN).

Presently preferred pH-sensitive aqueous-swellable hydrogels are copolymers of n-alkyl methacrylates (AMA) or methyl methacrylates (MMA) with N,N-dimethylaminoethyl methacrylate (DMA) or N,N-dimethylaminoethyl methacrylamide (DMAA) monomers, cross-linked with small amounts of divinyl benzene. A detailed description of a method of preparing these polymers may be had by reference to Example I, herein. The swelling properties and equilibrium hydration of these polymers may be modified by varying the molar ratios of the AMA or MMA to DMA or DMAA, or by varying the number of hydrocarbons in the AMA side chain. When the alkyl side chain length n is increased, the AMA becomes more hydrophobic and swelling of the hydrogel is reduced. In general, the preferred molar ratio of AMA or MMA monomers to DMA or DMAA monomers above about 86/14 (mole % AMA or MMA/mole % DMA or DMAA), preferably in the range of about 86/14 to about 60/40. MMA/DMA and MMA/DMAA copolymers having mole ratios of about 70/30 are particularly preferred.

Those skilled in the art will appreciate that the structural configuration of the self-regulated implantable pump of this invention can be varied considerably, and that the invention can be manifested in numerous forms and materials. For example, rather than utilizing a movable partition to separate the first and second chambers, the second chamber can be in the form of an elastomeric bladder or balloon. Suitable compositions for such a bladder or balloon include natural rubber, butyl rubber, latex rubber, plasticized polyurethanes, nylon, gelatin, polyvinyl alcohol, synthetic silicone elastomers and the like. The diaphragm may be composed of latex rubber and other similar materials such as those listed above. While a diaphragm between the second chamber and the water-swellable hydrogel member may be useful, it is not necessarily required or preferred, depending upon such variables as the strength and composition of the hydrogel member and the configuration and composition of the second chamber.

The pump is preferably configured to contain sufficient insulin for maintenance of the diabetic patient for one year, although it can be readily designed to provide shorter or longer periods of operation. One year duration of operation permits the reimplantation of pumps to occur at convenient one year time intervals and avoids the necessity of performing the implantation surgery on a more frequent basis. If a one year period of operability is desired, the insulin containing chamber should be configured to hold approximately 10 cc of an appropriate pharmaceutically acceptable insulin composition. Approximately 1 cc of insulin is sufficient to sustain a patient for one year. Assuming the diabetic patient ingests three meals per day, in one year a patient will require approximately 1000 "boosts" of insulin from the pump. If the volume of insulin formulation incorporated is 10 cc, then each boost of insulin has an average volume of about 10 microliters. The composition would contain about 10%–99% insulin, the remainder being pharmaceutically acceptable stabilizers, carriers and the like. Most of the volume of the pump would consist initially of the insulin formulation, and later of the aqueous body fluids or water that displaces it. Assuming a semisolid formulation, the volume of the pump can be on the order of 10 cc or less. This compares favorably to the volumes of proposed implantable electromechanical pumps, since the latter require motors and batteries. This volume is also satisfactory for implantation in the peritoneal cavity, which is a presently preferred site.

As shown in FIGS. 1A, 1B, 1C, the geometry of the pump may be cylindrical. This is a convenient geometry for both manufacture and implantation. Other geometries, such as spherical, cubical, square prismatic, and the like can of course be utilized if desired.

The glucose-sensitive reagent may be immobilized in the aqueous-swellable polymer member by covalent bonding, or by trapping the reagent molecules within the polymer chains. Mechanisms for immobilizing enzymes in polymers or on their surfaces are well known. In the case of both glucose oxidase and catalase, there are at least two ways the enzymes can be immobilized. One way is to bind the enzymes covalently to the pH-sensitive polymer. This may be accomplished by including the enzyme in the polymerization mixture, and irradiating the mixture with a Cobalt source as the polymerization proceeds. This method is described in some detail by Kost et al, J. Biomed. Mater. Res., 19, 1117 (1985). This procedure has the advantage that protons generated by the glucose/glucose oxidase/catalase reaction are in the immediate vicinity of the ionizable groups of the gel.

A second method is to cast a thin membrane consisting of a nonionizable hydrogel such as polyacrylamide or polyHEMA and the enzyme. The enzyme can be either bound covalently to the membrane, or "trapped" inside the membrane network. This membrane is in turn layered between the glucose solution (i.e., body fluids) and the pH-sensitive aqueous-swellable membrane. This technique is described in greater detail by Ishihara et al., Polymer J., 16, 625 (1984). This is a simple method to implement, and if the enzyme-containing membrane is sufficiently thin, diffusion of protons into the pH-sensitive hydrogel can occur rapidly.

When protons are generated by the reaction between blood glucose and the immobilized glucose oxidase, they can either diffuse to the polybasic groups and/or cross-links in the pH-sensitive gel, or out into the body in which the pump is implanted. The latter process reduces the efficiency of the mechanochemical transduction. (This will be true for either immobilization technique.) Thus, a technique for retarding proton back-diffusion is desirable. This may be accomplished by placing a thin, hydrated, positively-charged membrane between the body fluids and the glucose-sensitive aqueous-swellable member. Such a membrane will allow free passage of uncharged molecules such as glucose, but retards passage of positively-charged ions such as protons by Donnan exclusion. Negatively-charged ions such as gluconate can cross the membrane and exchange with buffer ions in the body fluids, such that electroneutrality is preserved on both sides of the membrane. It should be noted that proton back-diffusion is desirable when the device is not pumping insulin. It is precisely this back-diffusion that permits the pH-sensitive gel to discharge and deswell. Discharging may occur over a relatively long period. Therefore, the positively-charged membrane should preferably retard, but not completely stop proton back-diffusion.

The following examples are merely illustrative of the invention and should not be considered as limiting the scope of the invention in any way.

EXAMPLE 1

Preparation of 70/30 MMA/DMA Hydrogel

A. A cross-linked copolymer of methyl methacrylate (MMA) and N,N-dimethylaminoethyl methacrylate (DMA) in a mole ratio of 70/30 was prepared by radical bulk copolymerization between two silanized glass plates (13 cm ×13 cm) as follows:

A teflon spacer (0.27, 0.32, 0.38 or 0.84 mm thick) was inserted between the plates near the edges to provide a uniform internal cavity for the monomer solution, and the assembly was held together from the outside by metal clamps. The monomer solution consisted of MMA and DMA in the ratio 70/30 mole % in addition to azobisisobutyronitrile (AIBN) 0.5% w/w, and the tetrafunctional cross-linking reagent divinyl benzene (0.1% w/w). The comonomer solution was degassed by stirring under light vacuum for five minutes and then was injected into the cavity between the glass plates from a glass syringe fitted with a 24 gauge needle. The assembly was then incubated in a vertical position under an argon atmosphere at 60 C for 18 hours to facilitate complete polymerization. The solid copolymer slab was then separated from the glass plates with a razor blade and cut into 7.0 or 9.5 mm diameter circular discs using a punch. The discs were washed in methanol for several days and then in methanol/water (50/50 v/v) overnight. They were then dried, first at room temperature for 24 hours, and then at 50 C in vacuum for an additional 24 hours. The resulting disc thicknesses were virtually the same as the thickness of the spacer used, as measured with a micrometer. The composition of several copolymer discs was checked by elemental analysis which indicated that complete polymerization of the monomer feed solution had occurred. The glass transition temperature of the dry gel was determined to be 90.8 C (inflection temperature) using differential scanning calorimetry with a heating rate of 15 C/min.

B. Similarly, following the procedure described in Paragraph A above, but substituting 30 mole % N,N-dimethylaminoethyl methacrylamide (DMAA) for the DMA, a 70/30 MMA/DMAA copolymer is obtained having an ionizable monomer whose amine group has a lower ionization constant and higher pka than does DMA. In like manner, but replacing the hydrophobic monomer with a hydrophilic monomer such as hydroxyethyl methacrylate (HEMA) or hydroxypropyl methacrylate (HPMA), copolymers consisting of HEMA/DMA, HEMA/DMAA, HPMA/DMA and HPMA/DMAA are obtained.

The mole ratios of the copolymers described in this example, and those consisting of other potential monomers such as those set forth in the Detailed Description of the Preferred Embodiments, can be readily adjusted to modify the swelling properties of the copolymer.

C. Incorporation of Glucose Oxidase

Following the procedures described in Paragraph A above, but including glucose oxidase type VIII from *Aspergillus nigr* (12,500 U/g solid) in the mixture of monomers, the enzyme/monomer/cross-linker mixture is injected into the cavity between the glass plates. The plate assembly is then placed in a −70° C. cold storage box and allowed to freeze. It is subsequently irradiated in a $^{60}Co$ source with a dose of 0.25 Mrad. After irradiation, the plates are set in buffer solution and maintained at 4° C.-7° C. until easily separated. The resulting membrane is removed, washed, and dried if desired, as described in Paragraph A.

EXAMPLE 2

Determination of Equilibrium Swelling and Kinetic Swelling of the Hydrogel

Copolymer discs in triplicate (equilibrium studies) or duplicate (kinetic studies), which were prepared according to the procedure described in Example 1, above, were immersed in either 0.01 M citric acid buffer (pH 2.0–7.0) or 0.01 M phosphate buffer (pH >7.0) at 25 C. The total ionic strength of each buffer was adjusted to 0.1 M by the addition of a calculated amount of NaCl. Periodically, the discs were withdrawn from the buffer solution, the surface water removed by lightly blotting with a laboratory tissue, and weighed. The disc weights were individually monitored in this way until they reached a constant value. This typically required from several hours to three weeks depending on the pH. Swelling for the copolymer samples is expressed as the swelling ratio: (g water)/(g dry disc) and is calculated as $(W_s-W_d)/W_d$ where $W_s$ and $W_d$ are the fully swollen and dry disc weights, respectively. Equilibrium swelling values were always reproducible to within 2% (relative standard error). The kinetic experiments were conducted in a thermostated water bath with a total buffer volume of 2 liters. Vigorous stirring was maintained in the flask in order to eliminate the effects of boundary layer resistances.

FIG. 1V shows the swelling isotherm for the MMA/DMA and MMA/DMAA 70/30 mole % gels prepared according to Example 1 as a function of pH at 25° C. and a total ionic strength of 0.1 M. Citrate buffer (0.01 M) was used at and below pH 7.0, and phosphate buffer (0.01 M) was used above pH 7.0. From these data, it is apparent that the MMA/DMAA copolymer discs are highly swollen at pH 7, and that swelling increased further with decreasing pH. The MMA/DMA gels are relatively hydrophobic at and above pH 6.6, containing less than about 10% (w/w) water at equilibrium. At pH 6.6, the equilibrium water content of these gel discs discontinuously increases to about 70%, giving rise to a swollen hydrophilic gel.

FIG. V shows the kinetics of swelling and deswelling of MMA/DMA 70/30 mole % copolymer discs in response to step changes in pH in a pH region (5.0–6.0) where the gel is already quite swollen. As shown, swelling and deswelling of the gels in response to pH change are rapid and repeatable.

EXAMPLE 3

Manufacture of Self-Regulating Mechanochemical Insulin Pump

A. A cylindrical housing 5 cm in length with a circular internal base area of 2 $cm^2$ is prepared from a suitable rigid material such as polymethylmethacrylate. The cylinder is open at one end, closed at the opposite end, and has 2 openings for valve placement along its length. A latex rubber diaphragm is secured horizontally within the cylinder at one end, and an MMA/DMAA 70/30 mole % copolymer disc incorporating immobilized glucose oxidase (prepared as described in Example 1), .84 mm in thickness and the same diameter as the internal diameter of the cylinder, is placed between the diaphragm and an ionic exchange screen which caps the open end of the pump. Adjacent to the diaphragm on the other side is placed a flaccid material rubber balloon having a one-way, in-flow, pressure-sensitive valve which communicates with the outside of the pump at one opening in the cylinder wall. The balloon contains about 1 cc saline solution. Adjacent to the saline containing balloon at the far end of the cylinder, is another natural rubber balloon which contains about 10 cc of stabilized flowable insulin formulation comprising 10,000 USP insulin units dissolved or suspended in a buffered 5% polyethylene glycol 6000/water solution. The insulin-containing balloon has a one-way pressure-sensitive out-flow only valve which communicates with the outside of the pump at the second opening in the cylinder wall. The valve housings are sealed to the pump housing cylinder so that body fluids cannot enter the cylinder at either opening in the cylinder wall.

I claim:

1. An implantable pump for the delivery of insulin to a mammal in need thereof, said pump comprising a housing which supports within its walls:
   (a) an aqueous-swellable member which initiates an insulin pumping cycle by swelling in response to an increase in blood glucose level and terminates an insulin pumping cycle by deswelling in response to a decrease in blood glucose level, said member being exposed to the body fluids which surround the pump when implanted in a mammal;
   (b) a first chamber containing a pharmaceutically acceptable insulin composition and including a valve means which permits the outflow of the insulin composition; and
   (c) means coupled with said first chamber for causing insulin to be expelled from the first chamber in response to swelling of the aqueous-swellable member.

2. A pump according to claim 1 in which the aqueous-swellable member includes immobilized glucose oxidase.

3. A pump according to claim 1 in which the aqueous-swellable member comprises a pH-sensitive hydrogel membrane which swells in response to a decrease in pH by absorbing aqueous biological fluids.

4. A pump according to claim 3 in which the aqueous-swellable member includes immobilized glucose oxidase.

5. A pump according to claim 1 in which the means for causing insulin to be expelled from the first chamber comprises a second chamber.

6. A pump according to claim 5 in which said second chamber includes a valve means which permits an influx of body fluids as a function of the expulsion of insulin composition from the first chamber.

7. A pump according to claim 6 in which the second chamber is expandable.

8. A pump according to claim 1 in which the first chamber is collapsible, such that its internal volume is always substantially the same as the volume of the insulin composition it contains.

9. A pump according to claim 8 in which the means for causing insulin composition to be expelled from the first chamber comprises a second chamber.

10. A pump according to claim 9 in which said second chamber includes a valve means which permits an influx of body fluids as a function of the expulsion of insulin composition from the first chamber.

11. A pump according to claim 10 in which said second chamber is expandable.

12. A pump according to claim 11 in which said second chamber expands as a function of the expulsion of insulin composition from the first chamber.

13. A pump according to claim 12 in which the valve means of the first chamber comprises a pressure-responsive valve which permits the outflow of the insulin composition in response to an increase in pressure in the chamber and seals the chamber in response to a decrease in pressure in the chamber.

14. A pump according to claim 13 in which the valve means of the second chamber comprises a pressure-responsive valve which seals the chamber in response to an increase in pressure in the chamber, and permits an influx of body fluids in response to a decrease in pressure in the chamber.

15. A pump according to claim 14 in which the aqueous-swellable member comprises a pH-sensitive hydrogel membrane which swells in response to a decrease in pH by absorbing aqueous biological fluids.

16. A pump according to claim 15 in which the aqueous-swellable member includes immobilized glucose oxidase.

17. A pump according to claim 1 in which the aqueous-swellable member is a homopolymer or copolymer comprising monomers selected from the group consisting of n-alkyl acrylic acids and methacrylic acids, n-alkyl acrylates and methacrylates, and n-alkylacrylamids and methacrylamides, and the hydroxy- and amino-derivatives thereof.

18. An implantable pump for the delivery of insulin to a mammal in need thereof, said pump comprising an implantable, biocompatible housing of fixed volume which supports within its walls:
   (a) an aqueous-swellable hydrogel member which swells in response to an increase in blood glucose level and deswells in response to a decrease in blood glucose level, said member being exposed to the body fluids which surround the pump when implanted in a mammal;
   (b) means defining a first chamber for holding a pharmaceutically acceptable insulin formulation, including a valve means which permits the outflow of the insulin composition;
   (c) means defining a second chamber for coupling the swelling of the aqueous-swellable hydrogel member to the first chamber such that insulin composition is expelled from the first chamber in response to swelling of the aqueous-swellable hydrogel member.

19. A pump according to claim 18 in which the aqueous-swellable hydrogel member comprises a pH-sensitive hydrogel membrane which swells in response to a decrease in pH by absorbing aqueous biological fluids.

20. A pump according to claim 19 in which the pH-sensitive hydrogel membrane includes immobilized glucose oxidase.

21. A pump according to claim 18 in which the first chamber is collapsible, the second chamber is expandable, and the second chamber expands as function of the collapse of the first chamber.

22. A pump according to claim 21 in which the internal volume of the first chamber decreases as a function of the volume of insulin composition which is expelled.

23. A pump according to claim 22 in which the total combined volume occupied by the first and second chambers within the housing is always approximately the same when the pressure in both chambers equals the pressure of the environment external to the pump.

24. A pump according to claim 23 in which the second chamber includes a pressure-responsive valve means which seals the chamber in response to an increase in pressure in the chamber, and permits an influx of body fluids in response to a decrease in pressure in the chamber.

25. A pump according to claim 24 in which the aqueous-swellable hydrogel member comprises a pH-sensitive hydrogel membrane which swells in response to a decrease in pH by absorbing aqueous biological fluids.

26. A pump according to claim 25 in which the pH-sensitive hydrogel membrane includes immobilized glucose oxidase.

27. A pump according to claim 26 in which the influx of body fluids to the second chamber is of a volume approximately equal to the volume of insulin composition expelled from the first chamber.

28. A pump according to claim 27 in which the aqueous-swellable hydrogel member includes a means adjacent to said hydrogel member and the second chamber for causing an increase in pressure in the second chamber when the hydrogel member swells.

29. A pump according to claim 28 in which said means for causing an increase in pressure in the second chamber comprises a diaphragm situated between the hydrogel member and the second chamber.

30. A pump according to claim 29 in which the second chamber comprises an elastomeric bladder.

31. A pump according to claim 28 which includes a means adjacent to both the first and second chambers whereby an increase in pressure in the second chamber causes an increase in pressure in the first chamber.

32. A pump according to claim 31 in which said means for causing an increase in pressure in the first chamber comprises a movable partition situated between said first and second chambers.

33. A pump according to claim 18 in which the aqueous-swellable member is a homopolymer or copolymer comprising monomers selected from the group consisting of n-alkyl acrylic acids and methacrylic acids, n-alkyl acrylates and methacrylates, and n-alkylacrylamids and methacrylamides, and the hydroxy- and amino-derivatives thereof.

34. An implantable pump for the delivery of insulin to a mammal in need thereof, said pump comprising an implantable, biocompatible housing of fixed volume which supports within its walls:
(a) a first chamber containing a pharmaceutically acceptable insulin composition and including a pressure-responsive valve means which permits the outflow of the insulin composition in response to an increase in pressure in the chamber and seals the chamber in response to a decrease in pressure in the chamber; and
(b) a second chamber including a pressure-responsive valve means which seals the chamber in response to an increase in pressure in the chamber, and permits an influx of body fluids in response to a decrease in pressure in the chamber;
(c) an aqueous-swellable hydrogel member which initiates an insulin pumping cycle by swelling in response to an increase in blood glucose level and terminates an insulin pumping cycle by deswelling in response to a decrease in blood glucose level, said member being exposed to the body fluids which surround the pump when implanted in a mammal and including a coupling means adjacent to at least one of said first and second chambers such that swelling of the hydrogel member causes an increase in pressure in both chambers.

35. A pump according to claim 34 in which the pressure-responsive valve in the second chamber permits the influx of body fluids in a volume approximately equal to the volume of insulin composition expelled during each insulin pumping cycle.

36. A pump according to claim 34 in which the total combined volume occupied by the first and second chambers within the housing is always approximately the same when the pressure in both chambers equals the pressure of the environment external to the pump.

37. A pump according to claim 34 in which the internal volume of the first chamber is always approximately the same as the volume of the insulin composition it contains.

38. A pump according to claim 34 in which the aqueous-swellable hydrogel member comprises a pH-sensitive hydrogel membrane.

39. A pump according to claim 38 in which the aqueous-swellable hydrogel member includes immobilized glucose oxidase.

40. A pump according to claim 39 in which the aqueous-swellable hydrogel member includes immobilized catalase.

41. A pump according to claim 39 in which the pH-sensitive hydrogel membrane is a homopolymer or copolymer comprising monomers selected from the group consisting of n-alkyl acrylic acids and methacrylic acids, n-alkyl acrylates and methacrylates, and n-alkylacrylamids and methacrylamides, and the hydroxy and amino- derivatives thereof.

42. A pump according to claim 41 in which the pH-sensitive hydrogel membrane is a copolymer comprised of AMA or DMA monomers copolymerized with DMA or DMAA monomers.

43. A pump according to claim 34 in which the aqueous-swellable hydrogel member is a homopolymer or copolymer comprising monomers selected from the group consisting of n-alkyl acrylic acids and methacrylic acids, n-alkyl acrylates and methacrylates, and n-alkylacrylamids and methacrylamides, and the hydroxy and amino- derivatives thereof.

44. An implantable pump for the self-regulated delivery of insulin to a mammal in need thereof, said pump comprising an implantable, biocompatible housing of fixed volume, which supports within its walls:
(a) an aqueous-swellable hydrogel member which initiates an insulin pumping cycle by swelling in response to an increase in blood glucose level and terminates an insulin pumping cycle by deswelling in response to a decrease in blood glucose level, said member being exposed to the body fluids which surround the pump when implanted in a mammal;
(b) a first chamber containing a pharmaceutically acceptable insulin composition and including a pressure-responsive valve means which permits the outflow of the insulin composition in response to an increase in pressure in the chamber and seals the chamber in response to a decrease in pressure in the chamber, said chamber being configured such that its internal volume is always the same as the volume of the insulin composition it contains; and (c) a second chamber in intimate contact with said first chamber and in direct or indirect contact with said aqueous-swellable hydrogel member, such that swelling of the hydrogel member due to an increase in blood glucose level causes an increase in pressure in both the first and second chambers, said second chamber including a pressure-responsive valve means which seals the chamber in response to an increase in pressure in the chamber and permits an influx of body fluids in response to a decrease in pressure in the chamber in a volume equal to the volume of insulin composition expelled during each insulin pumping cycle, wherein the total combined volume occupied by the first and second chambers within the housing is always approximately the same when the pressure in both chambers substantially equals the pressure of the environment external to the pump.

* * * * *